United States Patent [19]

Hauck et al.

[11] 4,252,801
[45] Feb. 24, 1981

[54] MORPHOLINYL ACETAMIDE DERIVATIVES AND USE THEREOF

[75] Inventors: Frederic P. Hauck, Bridgewater; Glenn A. Jacobs, Princeton, both of N.J.

[73] Assignee: E. R. Squibb & Sons, Inc., Princeton, N.J.

[21] Appl. No.: 109,441

[22] Filed: Jan. 4, 1980

[51] Int. Cl.³ ............... A61K 31/535; A61K 31/54; C07D 265/30
[52] U.S. Cl. ............... 424/246; 424/248.51; 424/248.53; 424/248.54; 424/248.56; 424/248.57; 424/248.58; 544/121; 544/130; 544/131; 544/146; 544/152; 544/165; 544/167; 544/168; 544/82; 544/85; 544/86; 544/87; 544/58.4; 544/141; 260/243.3
[58] Field of Search ............ 544/168, 165, 167, 121, 544/130, 131, 146, 152, 58.4, 141, 82, 85, 86, 87; 260/243.3; 424/248.51, 248.53, 248.54, 248.56, 248.57, 248.58, 246

[56] References Cited

U.S. PATENT DOCUMENTS 3,658,806  4/1972  Denss et al. .................. 544/168

*Primary Examiner*—Henry J. Jiles
*Assistant Examiner*—R. W. Ramsuer
*Attorney, Agent, or Firm*—Lawrence S. Levinson; Burton Rodney

[57] ABSTRACT

Morpholinyl acetamide derivatives are provided having the structure

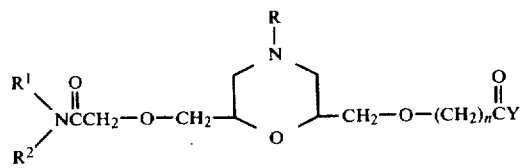

wherein R is hydrogen, lower alkyl, lower alkenyl or lower alkanoyl, $R^1$ and $R^2$ may be the same or different and are lower alkyl, lower alkenyl, phenyl-lower alkyl or lower alkoxy, or

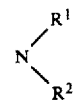

may be taken together to form a 5- to 7-membered heterocyclic ring optionally containing one other hetero atom, such as nitrogen, sulfur or oxygen; Y is hydroxyl, OR wherein R is as defined above, or

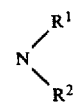

wherein $R^1$ and $R^2$ and $R^1$ and $R^2$ taken together with the nitrogen to which they are attached are as defined above, and n is 1 to 6.

These compounds are useful as anti-arrhythmia agents and have been found to be effective in the treatment of acute myocardial infarction.

10 Claims, No Drawings

MORPHOLINYL ACETAMIDE DERIVATIVES AND USE THEREOF

DESCRIPTION OF THE INVENTION

The present invention relates to compounds which are useful in treating arrhythmia and acute myocardial infarction and have the formula

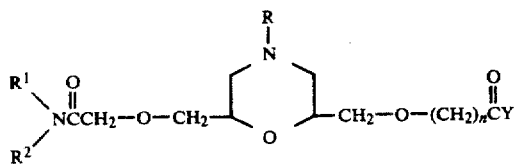

wherein R is hydrogen, lower alkyl, lower alkenyl, phenyl-lower alkyl, monocyclic aroyl, lower alkanoyl, or monocyclic heterocyclic containing one hetero atom, namely, O, N or S.

$R^1$ and $R^2$ are the same or different and are lower alkyl, lower alkenyl, phenyl-lower alkyl, or lower alkoxy-lower alkyl, or $R^1$ and $R^2$ taken together with the nitrogen to which they are attached may form a 5-, 6- or 7-membered heterocyclic ring optionally containing one other hetero atom, such as nitrogen, sulfur or oxygen;

Y is hydroxyl, OR wherein R is as defined above, or

wherein $R^1$, $R^2$, and $R^1$ and $R^2$ taken together with the nitrogen to which they are attached, are as defined above; and n is an integer from 1 to 6.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "lower alkanoyl" refers to any of the above lower alkyl groups attached to a carbonyl group

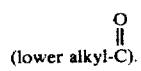

The term "lower alkoxy" refers to any of the above lower alkyl groups attached to an oxygen (lower alkyl-O).

The term "monocyclic aroyl" as employed herein refers to monocyclic carbocyclic aryl radicals, for example, phenyl, linked to a carbonyl group, the phenyl being unsubstituted or substituted with one, two or three lower alkyl groups, halogen, hydroxy, amino or nitro.

The term "monocyclic aromatic heterocyclic" as used herein includes mono hetero 5- or 6-membered rings containing one hetero atom, namely, O, S, or N, such as, furan, pyridine and thiophene.

As indicated, the group

may form a heterocyclic radical containing in addition to nitrogen, one other heteroatom, such as nitrogen, oxygen or sulfur, and may contain up to 6 carbons.

Illustrative of the heterocyclic radicals represented by

are the following: piperidino; (lower alkyl)piperidino [e.g., 2-, 3-, or 4-(lower alkyl)piperidino, such as 2-(ethyl)piperidino] or di(lower alkyl)piperidino [e.g., 2,4-, 2,5- or 3,5-di(lower alkyl)piperidino such as 2,4-dimethylpiperidino or 2,5-di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethylpiperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino [e.g., 3,5-dimethylmorpholino]; (lower alkoxy)morpholino [e.g., 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino]; (lower alkoxy)thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperazino or 2,6-dimethylpiperazino]; (lower alkoxy)piperazino [e.g., 2-methoxypiperazino]; (hydroxy-lower alkyl)-piperazino [e.g., $N^4$-(2-hydroxyethyl)piperazino]; (alkanoyloxy-lower alkyl)piperazino wherein the alkanoyloxy group has up to 14 carbons [e.g., $N^4$-(2-heptanoyloxyethyl)piperazino or $N^4$-(2-dodecanoyloxyethyl)piperazino]; (hydroxy-lower alkoxy-lower alkyl)-piperazino [e.g., (hydroxy-methoxy-methyl)-piperazino]; (carbo-lower alkoxy)piperazino [e.g., $N^4$-(carbomethoxy-, carboethoxy-, or carbopropoxy)-piperazino]; homopiperazino; or $N^4$-(hydroxy-lower alkyl)homopiperazino [e.g., $N^4$-(2-hydroxyethyl)-homopiperazino].

The compounds of formula I form acid-addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts, such as phosphate, sulfate, nitrate, etc., organic acid salts, such as oxalate, tartrate, malate, maleate, citrate, pamoate, fumarate, camphosulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is intereacted with at least one equivalent of the desired alkylating agent.

The compounds of formula I include all stereoisomers and mixtures thereof.

Preferred are those compounds of formula I wherein $R^1$ and $R^2$ are each lower alkyl, such as n-propyl, Y is

wherein $R^1$ and $R^2$ are each lower alkyl, such as n-propyl, R is lower alkyl, such as n-butyl, and n is 1.

The compounds of formula I may be prepared according to the following reaction sequence.

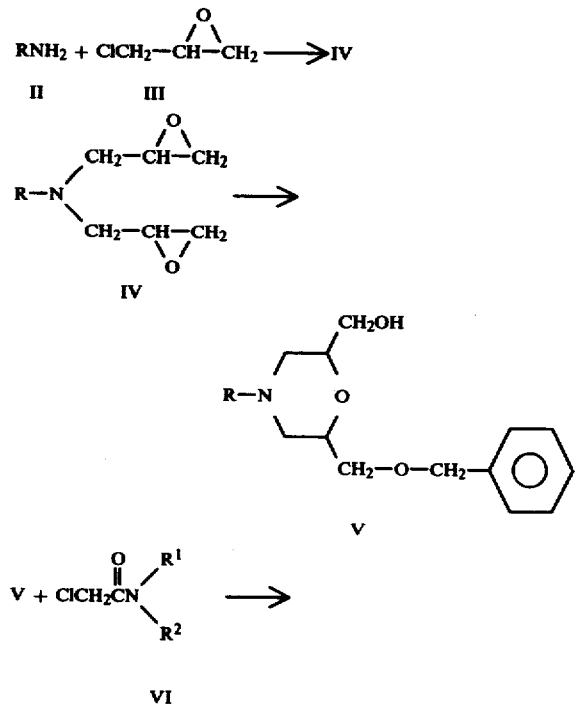

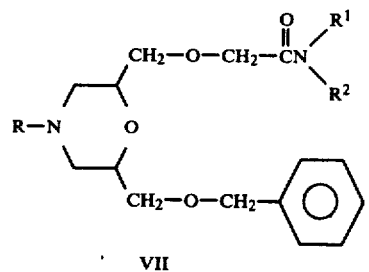

VII

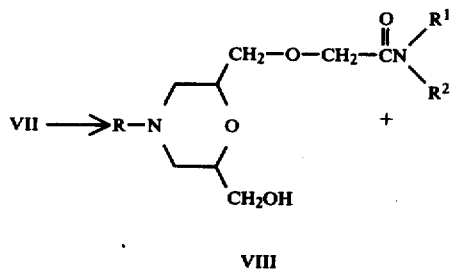

VIII

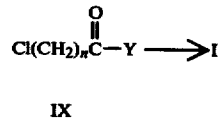

IX

In carrying out the above reactions, the amine II is reacted with epichlorohydrin III in a molar ratio of II:III of within the range of from about 0.2:1 to about 1:1, and preferably from about 0.4:1 to about 0.8:1, at a temperature of within the range of from about 20° to about 40° C., and preferably from about 25° to about 35° C., for a period of from about 0.5 to about 8 hours or more. The reaction mixture is cooled to below room temperature, and a strong base medium, such as sodium hydroxide or potassium hydroxide is added while keeping the reaction temperature preferably below 28° C. The N,N-bis(2,3-epoxypropyl)amine IV is separated out and reacted with a mixture of benzyl alcohol and sodium to form the benzyloxymethyl compound V. The N,N-bis(2,3-epoxypropyl)amine IV is employed in a molar ratio to benzyl alcohol of within the range of from about 0.5:1 to about 1.5:1, and preferably from about 0.7:1 to about 1.2:1, and the reaction is carried out at a temperature of within the range of from about 80° to about 140° C., for a period of from about 1 to about 12 hours.

Compound V is then reacted with amide VI in the presence of an inert solvent, such as dimethylsulfoxide and a hydrogenating agent, such as sodium hydride to form the compound of structure VII. The above reaction may be carried out at ambient temperature, employing a molar ratio of V:VI of within the range of from about 0.5:1 to about 4:1, and preferably from about 1:1 to about 2:1, for periods of from 15 minutes up to 2 hours or more.

The formula VII compound is then reduced to the formula VIII compound in the presence of an organic acid, such as acetic acid and a hydrogenation catalyst, such as palladium on charcoal or platinum oxide.

The compound VIII is then reacted with compound IX (molar ratio of VIII:IX of within the range of from about 0.5:1 to about 4:1, and preferably from about 1:1 to about 2:1), in the presence of an inert solvent, such as dimethylsulfoxide, dioxane, glyme or diglyme, and sodium hydride to form the formula I compounds of the invention.

In addition, in accordance with the present invention, there is provided a number of novel intermediates, namely compounds of the formula V

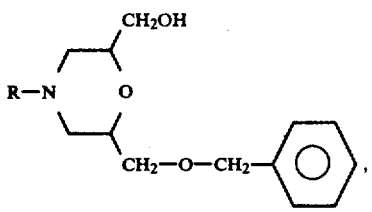

compounds of the formula VII

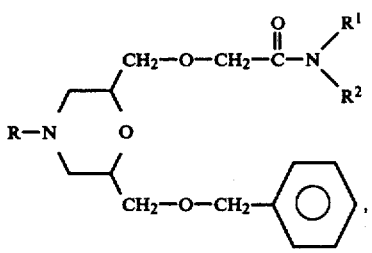

and compounds of the formula VIII

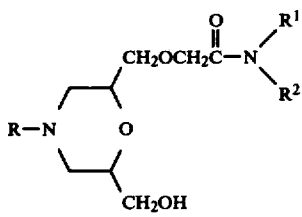

In the above formulae, R, R¹, R² and

are as defined hereinbefore with respect to the compounds of formula I.

The compounds of formula I have anti-arrhythmic activity as indicated by A. S. Harris, in "Delayed Development of Ventricular Ectopic Rhythms Following Experimental Coronary Occlusion" *Circulation* 1:1318–1328, 1950 and are useful in the treatment of arrhythmia in mammalian species, for example, rats and dogs. In addition, the compounds of formula I have been found to be effective in treating acute myocardial infarction as indicated by the test described by A. S. Harris, supra. A compound of formula I (below) as well as its physiologically acceptable acid salts may be compounded according to pharmaceutical practice in oral or parenteral dosage forms, such as tablets, capsules, elixirs, injectables or powders for administration of about 100 mg of 400 mg per day, preferably 125 mg to 175 mg per day, in 2 to 4 divided doses.

The following Examples represent preferred embodiments of the present invention. Unless otherwise indicated, all temperatures are expressed in degrees Centigrade.

EXAMPLE 1

4-Butyl-6-[(phenylmethoxy)methyl]-2-morpholinemethanol

A. N,N-Bis(2,3-epoxypropyl)butylamine

An amount of 200 g of epichlorohydrin (2.16 mole) is kept at 28°–32° while 73 g of redistilled n-butylamine (1.0 mole) is added with stirring and the reaction then maintained at 30° for 4 hours. The mixture is then cooled to 20° and 300 ml of 50% sodium hydroxide solution is added during a ½ hour period, keeping the reaction temperature between 20°–25°. The reaction is then allowed to stir for 3 hours after which time the mixture is diluted with 300 ml of water to dissolve the NaCl generated during the reaction. The upper layer is separated and washed with 100 ml of 50% NaOH, separated and vacuum distilled yielding 140 g of crude product, b.p. 95°–120° @0.4 mm. The crude material is then redistilled yielding 109 g (60%) of the title compound, b.p. 112°–116° @0.4 mm. I.R. and N.M.R. are consistent with the structure. (Lit. ref. Houben-Weyl, Vol. 14, Part 2, p. 544).

B. 4-Butyl-6-[(phenylmethoxy)methyl]-2-morpholinemethanol

An amount of 125 g of benzyl alcohol is stirred and 0.3 g of finely cut sodium metal (0.013 mole) is added and the mixture then stirred under nitrogen for 2.5 hours. Then with stirring, 27.79 g of N,N-bis(2,3-epoxypropyl)benzylamine (0.15 mole) is added to the reaction mixture and stirring at room temperature continued for 0.5 hour, followed by heating the mixture at reflux for 16 hours. The mixture is then cooled to room temperature and poured into 400 ml of water. The aqueous mixture is extracted with 2×250 ml portions of chloroform, and the $CHCl_3$ extracts are combined and dried over anhydrous sodium sulfate. The $CHCl_3$ is removed in vacuo and the colorless oil vacuum distilled through a 10 cm vigreux distilling column. The fraction distilling at b.p. 196°–199° @0.4 mm is collected yielding 28.6 g (65%) of the title compound.

EXAMPLE 2

2-[[4-Butyl-6-[(phenylmethoxy)methyl]-2-morpholinyl]methoxy]-N,N-dipropylacetamide A mixture of 16.2 g of 4-butyl-6-[(phenylmethoxy)methyl]-2-morpholinemethanol (0.055 mole) and 9.81 g of 2-chloro-N,N-dipropylacetamide (0.055 mole) are dissolved in 200 ml of dry dimethyl sulfoxide and the mixture stirred at room temperature under nitrogen. Slowly, 1.0 g of sodium hydroxide (0.04 mole) is added to the dimethyl sulfoxide mixture and the reaction allowed to stir at ambient temperature (23°). After stirring for 10 minutes an exothermic reaction begins to take place and an ice-bath is used to maintain the reaction temperature below 30°. After stirring for 1 hour the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The $CHCl_3$ extracts are combined and washed with 4×300 ml portions of water. The $CHCl_3$ layer is separated, dried over anhydrous $Na_2SO_4$, and the $CHCl_3$ removed in vacuo yielding 22.4 g (94%) of the title compound as a yellow oil. The resulting oil is purified on a neutral Alumina III column (500 g), 40% chloroform/hexane yielding 12.9 g (54%) of product as a pale yellow oil. The 12.9 g of product are dried in vacuo (80° @0.2 mm) to give the desired product.

EXAMPLE 3

2-[[4-Butyl-6-(hydroxymethyl)-2-morpholinyl]methoxy]-N,N-dipropylacetamide

To a solution of 10.86 g of 2-[[4-butyl-6-[(phenylmethoxy)methyl]-2-morpholinyl]methoxy]-N,N-dipropylacetamide (0.025 mole) in 125 ml of glacial acetic acid is added 4.0 g of 10% Pd/C and the mixture is hydrogenated at 50 psi at 60° over a period of 28 hours (debenzylation taking up 94% of the calculated theory). The mixture is cooled to room temperature and the Pd/C removed via filtration through a pad of "celite" filter aid. The acetic acid is removed in vacuo yielding a pale yellow oil. The oil is taken up in 200 ml of chloroform and washed with 100 ml of saturated NaHCO$_3$ solution. The CHCl$_3$ layer is separated, dried over anhydrous Na$_2$SO$_4$ and then the CHCl$_3$ is removed in vacuo yielding 8.2 g (95%) of crude product as a dark brown oil. The oil is chromatographed on 150 g of neutral Alumina III to give 0.5 g of forerun (eluted with 100 ml of chloroform) and 7.6 g (88%) of the desired product (eluted with 400 ml of chloroform and 200 ml of 2% methanolic chloroform). The 7.6 g of product is dried in vacuo to give the desired product, a dense yellow-orange oil.

EXAMPLE 4

2,2'-[(4-Butyl-2,6-morpholinediyl)bis(methoxy)]-bis[N,N-dipropylacetamide]

A mixture of 6.3 g of 2-[[4-butyl-6-(hydroxymethyl)-2-morpholinyl]methoxy]-N,N-dipropylacetamide (0.0183 mole) and 3.25 g of 2-chloro-N,N-dipropylacetamide (0.0183 mole) is dissolved in 100 ml of dry dimethyl sulfoxide and the mixture stirred at room temperature under nitrogen. Slowly, 0.88 g of sodium hydride (0.0183 mole; 50% oil dispersion) is added to the dimethyl sulfoxide mixture and the reaction allowed to stir at ambient temperature (22°). After stirring for 10 minutes, an exothermic reaction begins to take place and an ice-bath is used to maintain the reaction temperature below 30°. After stirring for ½ hour, the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The CHCl$_3$ extracts are combined and washed with 6×300 ml portions of water. The CHCl$_3$ layer is separated and dried over anhydrous Na$_2$SO$_4$ overnight. The CHCl$_3$ is removed in vacuo yielding 6.30 g (71%) of title compound as a dark yellow oil. The resulting oil is purified on a neutral Alumina III column (200 g), 2% methanol/chloroform, yielding 5.12 g (58%) of title compound as a pale yellow oil. Tlc on alumina CHCl$_3$ with 2% methanol is single spot.

EXAMPLES 5 to 15

Following the procedure of Example 1 except substituting for n-butylamine, the amine shown in Column I of Table A set out below, the novel intermediate shown in Column II is obtained.

TABLE A

| Ex. No. | Column I<br>R—NH$_2$<br>R | Column II<br>(R—N morpholine with CH$_2$OH and CH$_2$—O—CH$_2$—C$_6$H$_5$)<br>R |
|---|---|---|
| 5. | C$_6$H$_5$CH$_2$— | as in Column I |
| 6. | C$_2$H$_5$— | |
| 7. | CH$_2$=CHCH$_2$— | |
| 8. | CH$_3$— | |
| 9. | i-C$_3$H$_7$— | |
| 10. | CH$_3$CH=CH—CH$_2$— | |
| 11. | n-C$_3$H$_7$ | |
| 12. | i-C$_4$H$_9$ | |
| 13. | CH$_2$=CH—CH$_2$CH$_2$— | |
| 14. | n-C$_5$H$_{11}$— | |
| 15. | CH$_3$CH$_2$CH=CH—CH$_2$— | |

EXAMPLES 16 to 26

Following the procedure of Example 2, except substituting for 4-butyl-6-[(phenylmethoxy)methyl]-2-morpholinemethanol, the intermediates of Examples 5 to 15 (shown in Column I of Table B below), and substituting for 2-chloro-N,N-dipropylacetamide, the amide shown in Column II, the novel intermediate shown in Column III is obtained.

TABLE B

| | Column I | Column II | Column III | |
|---|---|---|---|---|
| | R—N(morpholine with CH₂OH at 2-position and CH₂—O—CH₂—C₆H₅ at 6-position) | ClCH₂C(=O)N(R¹)(R²) | R—N(morpholine with CH₂—O—CH₂C(=O)N(R¹)(R²) at 2-position and CH₂OCH₂—C₆H₅ at 6-position) | |
| Ex. No. | R | N(R¹)(R²) | R | N(R¹)(R²) |
| 16. | $C_6H_5CH_2-$ | $N(CH_3)(CH_3)$ | as in Column I | as in Column II |
| 17. | $C_2H_5$ | $N(C_2H_5)(CH_3)$ | | |
| 18. | $CH_2=CHCH_2-$ | $N(CH_2CH=CH_2)(CH_2CH=CH_2)$ | | |
| 19. | $CH_3$ | $N(CH_3)(CH_2-CH=CH_2)$ | | |
| 20. | $i\text{-}C_3H_7$ | $N(CH_2C_6H_5)(CH_2C_6H_5)$ | | |
| 21. | $CH_3CH=CH-CH_2$ | $N(C_2H_4OCH_3)(C_2H_4OCH_3)$ | | |
| 22. | $n\text{-}C_3H_7$ | —N(pyrrolidinyl) | | |
| 23. | $i\text{-}C_4H_9$ | —N(piperidinyl) | | |
| 24. | $CH_2=CH-CH_2CH_2-$ | —N(N′-methylpiperazinyl) | | |
| 25. | $n\text{-}C_5H_{11}$ | —N(morpholinyl) | | |
| 26. | $CH_3CH_2CH=CH-CH_2-$ | —N(thiomorpholinyl) | | |

EXAMPLES 27 to 37

Following the procedure of Example 3, except substituting for 2-[[4-butyl-6-[(phenylmethoxy)methyl]-2-morpholinyl]methoxy]-N,N-dipropylacetamide, the intermediates of Examples 16 to 26 (shown in Column I of Table C below), the novel intermediate shown in Column II is obtained.

TABLE C

| | Column I | Column II |
|---|---|---|
| | ![structure with CH₂OCH₂C₆H₅] | ![structure with CH₂OH] |

| Ex. No. | R | N(R¹)(R²) | R | N(R¹)(R²) |
|---|---|---|---|---|
| 27. | C₆H₅CH₂ | N(CH₃)(CH₃) | as in Column I | as in Column II |
| 28. | C₂H₅ | N(C₂H₅)(CH₃) | | |
| 29. | CH₂=CHCH₂— | N(CH₂CH=CH₂)(CH₂CH=CH₂) | | |
| 30. | CH₃ | N(CH₃)(CH₂—CH=CH₂) | | |
| 31. | i-C₃H₇ | N(CH₂C₆H₅)(CH₂C₆H₅) | | |
| 32. | CH₃CH=CH—CH₂ | N(C₂H₄OCH₃)(C₂H₄OCH₃) | | |
| 33. | n-C₃H₇ | —N(azetidinyl) | | |
| 34. | i-C₄H₉ | —N(piperidinyl) | | |
| 35. | CH₂=CH—CH₂CH₂— | —N(N'-methylpiperazinyl) | | |
| 36. | n-C₅H₁₁ | —N(morpholinyl) | | |
| 37. | CH₃CH₂CH=CH—CH₂— | —N(thiomorpholinyl) | | |

EXAMPLES 38 to 48

Following the procedure of Example 4, except substituting for 2-[[4-butyl-6-(hydroxymethyl)-2-morpholinyl]methoxy]-N,N-dipropylacetamide, the intermediates of Examples 27 to 37 (shown in Column I of Table D below), and substituting for 2-chloro-N,N-dipropylacetamide, the amide shown in Column II, the product shown in Column III is obtained.

TABLE D

| | Column I | | Column II | Column III | | |
|---|---|---|---|---|---|---|
| Ex. No. | R | $N{<}^{R^1}_{R^2}$ | $(CH_2)_n\overset{O}{\underset{\|}{C}}{-}Y$ | R | $N{<}^{R^1}_{R^2}$ | $(CH_2)_n\overset{O}{\underset{\|}{C}}{-}Y$ |
| 38. | $C_6H_5CH_2$ | $N{<}^{CH_3}_{CH_3}$ | $\overset{O}{\underset{\|}{CH_2COH}}$ | as in Column I | | as in Column II |
| 39. | $C_2H_5$ | $N{<}^{C_2H_5}_{CH_3}$ | $(CH_2)_2\overset{O}{\underset{\|}{C}}OCH_3$ | | | |
| 40. | $CH_2{=}CHCH_2{-}$ | $N{<}^{CH_2CH=CH_2}_{CH_2CH=CH_2}$ | $(CH_2)_3\overset{O}{\underset{\|}{C}}\overset{O}{\underset{\|}{OC}}CH_3$ | | | |
| 41. | $CH_3$ | $N{<}^{CH_3}_{CH_2-CH=CH_2}$ | $(CH_2)_4\overset{O}{\underset{\|}{C}}OCH_2{=}CHCH_3$ | | | |
| 42. | $i\text{-}C_3H_7$ | $N{<}^{CH_2C_6H_5}_{CH_2C_6H_5}$ | $(CH_2)_5\overset{O}{\underset{\|}{C}}N{<}^{CH_3}_{CH_3}$ | | | |
| 43. | $CH_3CH{=}CH{-}CH_2{-}$ | $N{<}^{C_2H_4OCH_3}_{C_2H_4OCH_3}$ | $CH_2\overset{O}{\underset{\|}{C}}N{<}^{CH_2CH=CH_2}_{CH_2CH=CH_2}$ | | | |
| 44. | $n\text{-}C_3H_7$ | 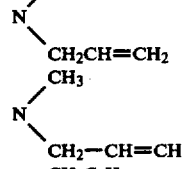 | 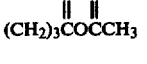 | | | |
| 45. | $i\text{-}C_4H_9$ | 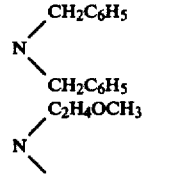 | 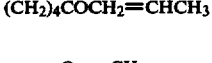 | | | |
| 46. | $CH_2{=}CH{-}CH_2CH_2{-}$ | 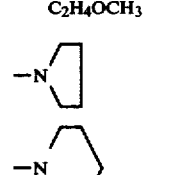 | 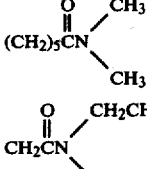 | | | |
| 47. | $n\text{-}C_5H_{11}$ | 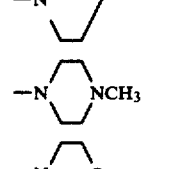 | 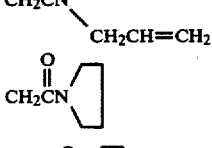 | | | |
| 48. | $CH_3CH_2CH{=}CH{-}CH_2{-}$ | 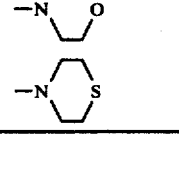 | 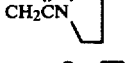 | | | |

EXAMPLE 49

2-[[6-[(Phenylmethoxy)methyl]-2-morpholinyl]methoxy]-N,N-dipropylacetamide

A. 6-[(Phenylmethoxy)methyl]-4-(phenylmethyl)-2-morpholinemethanol 5.48 G (0.025 mole) of N,N-bis(2,3-epoxypropyl)benzylamine is added to a mixture of 2.70 g (0.025 mole) of benzyl alcohol in 75 ml of dioxane containing 1 equivalent of sodium hydride. The reaction is allowed to cool below 40° with an ice-bath for approximately ½ hour and is then heated at reflux overnight. After cooling to room temperature, the entire mixture is poured slowly, with stirring, into 150 ml of water. The aqueous mixture is extracted with 3×125 ml portions of chloroform. The CHCl₃ extracts are combined, washed with 200 ml of water and 200 ml of saturated NaCl solution. The CHCl₃ layer is then dried over anhydrous NaSO₄, evaporated in vacuo to yield 6.1 g (74%) of crude product as a pale yellow oil. The oil is chromatographed on 300 g of neutral Alumina III to give 5.6 g (68%) of 6-[(phenylmethoxy)methyl]-4-(phenylmethyl)-2-morpholinemethanol.

B. 2-[[6-[(Phenylmethoxy)methyl]-4-(phenylmethyl)-2-morpholinyl]methoxy]-N,N-dipropylacetamide A mixture of 4.9 g (0.015 mole) of 6-[(phenylmethoxy)methyl]-4-(phenylmethyl)-2-morpholinemethanol and 2.84 g (0.016 mole) of 2-chloro-N,N-dipropylacetamide are dissolved in 100 ml of dry DMSO and the mixture stirred at room temperature under nitrogen. Slowly, 0.88 g of sodium hydride (0.0183 mole, 50% oil dispersion) is added to the DMSO mixture and the reaction allowed to stir at ambient temperature (22°). After stirring for 10 minutes, an exothermic reaction begins to take place and an ice-bath is used to maintain the reaction temperature below 30°. After stirring for ½ hour, the ice-bath is removed and the reaction allowed to stir at room temperature for 18 hours. The excess NaH is destroyed by adding 5 ml of methanol and the entire reaction mixture is then poured into 400 ml of water. The product is extracted and washed with 6×300 ml portions of water. The product is then extracted with 3×125 ml portions of chloroform. The CHCl$_3$ extracts are combined and washed with 6×300 ml portions of water. The CHCl$_3$ layer is separated and dried over anhydrous Na$_2$SO$_4$ overnight. The CHCl$_3$ is removed in vacuo yielding the crude product as a dark oil. The resulting oil is purified on a neutral Alumina III column (200 g), eluting with 2% methanol/chloroform, yielding 4.6 g (69%) of the desired product, 2-[[6-[(phenylmethoxy)methyl]-4-(phenylmethyl)-2-morpholinyl]methoxy]-N,N-dipropylacetamide.

C. 2-[[6-[(Phenylmethoxy)methyl]-2-morpholinyl]methoxy]-N,N-dipropylacetamide A solution of the compound produced in part B, 3.27 g, (0.01 mole) in glacial acetic acid with 4.0 g of 5% Pd/C is hydrogenated at 50 psi over a period of 2 hours. The mixture is cooled to room temperature and the Pd/C removed via filtration through a pad of "celite" filter aid. The acetic acid is removed in vacuo yielding a pale yellow oil. The oil is chromatographed on 150 g of neutral Alumina III, eluting with 10% methanol/chloroform, to yield 2.81 g (74%) of the desired product, 2-[[6-[(phenylmethoxy)methyl]-2-morpholinyl]methoxy]-N,N-dipropylacetamide.

EXAMPLE 50

2-[[4-Acetyl-6-[(phenylmethoxy)methyl]-2-morpholinyl]methoxy]-N,N-dipropylacetamide A mixture of the Example 49 product (2.5 g, 0.0066 mole) and 15 ml of acetic anhydride is allowed to stir at room temperature for 4 hours and is then carefully poured into 50 ml of ice water with rapid stirring. The mixture is extracted with 3×50 ml portions of chloroform and the extracts combined. The combined CHCl$_3$ extracts are washed with 100 ml of 10% sodium bicarbonate solution, followed by washing with 100 ml of saturated sodium chloride solution. The chloroform mixture is then dried over anhydrous sodium sulfate and the CHCl$_3$ removed in vacuo yielding 2.61 g (94%) of the crude product as an oily residue. The resulting oil is chromatographed on 150 g of neutral Alumina III, eluting with chloroform/ether (3:1) yielding 2.48 g (89%) of the title compound as a pale yellow solid.

EXAMPLE 51

2-[[4-Acetyl-6-(hydroxymethyl)-2-morpholinyl]methoxy]-N,N-dipropylacetamide To a solution of 2.40 g (0.0057 mole) of the Example 50 product in 125 ml of glacial acetic acid is added 4.0 g of 10% Pd/C and the mixture is hydrogenated at 50 psi at 60° over a period of 28 hours (debenzylation taking up 94% of the calculated theory). The mixture is cooled to room temperature and the Pd/C removed via filtration through a pad of "celite" filter aid. The acetic acid is removed in vacuo yielding a pale yellow oil. The oil is taken up in 200 ml of chloroform and washed with 100 ml of saturated NaHCO$_3$ solution. The CHCl$_3$ layer is separated, dried over anhydrous Na$_2$SO$_4$ and then the CHCl$_3$ is removed in vacuo yielding 1.86 g (97%) of crude product as a yellow oil. The oil is chromatographed on 150 g of neutral Alumina III, eluted with 5% methanol in chloroform yielding 1.62 g (86%) of the desired product as a dense yellow-orange oil.

EXAMPLE 52

2,2'-[(4-Acetyl-2,6-morpholinediyl)dimethoxy]bis[N,N-dipropylacetamide]

A mixture of 1.5 g (0.0045 mole) of the Example 51 product and 0.76 g of 2-chloro-N,N-dipropylacetamide (0.00465 mole) are dissolved in 100 ml of dry DMSO and the mixture stirred at room temperature under nitrogen. Slowly, 0.44 g of sodium hydride (0.009 mole; 50% oil dispersion) is added to the DMSO mixture and the reaction allowed to stir at ambient temperature (22°). After stirring for 10 minutes an exothermic reaction begins to take place and an ice-bath is used to maintain the reaction temperature below 30°. After stirring for ½ hour the ice-bath is removed and the reaction allowed to stir at room temperature for 18 hours. The excess NaH is destroyed by adding 5 ml of methanol and the entire reaction mixture is then poured into 400 ml of water. The product is extracted with 3×125 ml portions of chloroform. The CHCl$_3$ extracts are combined and washed with 6×300 ml portions of water. The CHCl$_3$ layer is separated and dried over anhydrous Na$_2$SO$_4$ overnight. The CHCl$_3$ is removed in vacuo yielding 1.5 g (71%) of product as a dark yellow oil. The resulting oil is purified on a neutral Alumina III column (200 g), 2% methanol/chloroform, yielding 1.12 g (52%) of the title product as a pale yellow oil.

EXAMPLES 53 to 56

Employing the procedure of Example 50 except substituting for acetic anhydride the reagent shown in Column I of Table E below, dissolved in pyridine, the product shown in Column II is obtained.

TABLE E

| Column I | Column II |
|---|---|
| R—Cl | 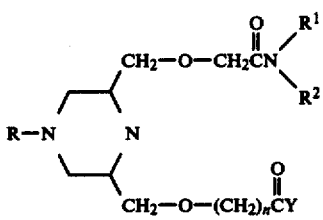 |
| Ex.  R | R as in Column I |
| 53. C₆H₅—C(=O)— | |
| 54. (furan-2-yl)—C(=O)— | |
| 55. (pyridin-3-yl)—C(=O)— | |
| 56. (thiophen-3-yl)—C(=O)— | |

What is claimed is:

1. A compound having the structure

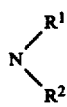

wherein R is hydrogen, lower alkyl, phenyl-lower alkyl, monocyclic aroyl, lower alkenyl, lower alkanoyl, or monocyclic aromatic heterocyclic containing one heteroatom;

$R^1$ and $R^2$ may be the same or different and are lower alkyl, lower alkenyl, phenyl lower alkyl, or lower alkoxy or

may be taken together to form a 5- to 7-membered heterocyclic ring optionally containing one other hetero atom, Y is hydroxyl, OR or

wherein R, $R^1$, $R^2$ and

are as defined above, and n is an integer from 1 to 6, and pharmaceutically acceptable acid addition salts thereof.

2. The compound of claim 1 wherein R is lower alkyl.

3. The compound of claim 1 wherein $R^1$ and $R^2$ are each lower alkyl.

4. The compound of claim 1 wherein n is 1 or 2 and Y is

5. The compound of claim 4 wherein Y is di(lower alkyl)amino.

6. The compound of claim 5 wherein R is lower alkyl, $R^1$ and $R^2$ are each lower alkyl, n is 1 and Y is di(lower alkyl)amino.

7. The compound of claim 6 having the name 2,2'-[(4-butyl-2,6-morpholinediyl)bis(methoxy)]bis[N,N-dipropylacetamide].

8. The compound of claim 6 having the name 2,2'-[(4-acetyl-2,6-morpholinediyl)bis(methoxy)]bis[N,N-dipropylacetamide].

9. A pharmaceutical composition for use in treating arrhythmia comprising an anti-arrhythmia effective amount of a compound as defined in claim 1 and a pharmaceutically acceptable carrier therefor.

10. A method for treating arrhythmia in mammals which comprises administering to a mammalian host an anti-arrhythmia effective amount of a compound as defined in claim 1.

* * * * *